(12) United States Patent
Kim et al.

(10) Patent No.: US 11,034,818 B2
(45) Date of Patent: Jun. 15, 2021

(54) ESTER-BASED COMPOUND, COMPOSITION COMPRISING THE SAME, METHOD FOR PREPARING THE SAME AND RESIN COMPOSITION COMPRISING THE SAME

(71) Applicant: LG CHEM, LTD., Seoul (KR)

(72) Inventors: Hyun Kyu Kim, Daejeon (KR); Mi Yeon Lee, Daejeon (KR); Jeong Ju Moon, Daejeon (KR); Joo Ho Kim, Daejeon (KR); Seok Ho Jeong, Daejeon (KR)

(73) Assignee: LG CHEM LTD., Seoul (KR)

( * ) Notice: Subject to any disclaimer, the term of this patent is extended or adjusted under 35 U.S.C. 154(b) by 14 days.

(21) Appl. No.: 15/546,185

(22) PCT Filed: May 12, 2016

(86) PCT No.: PCT/KR2016/005039
§ 371 (c)(1),
(2) Date: Jul. 25, 2017

(87) PCT Pub. No.: WO2016/182377
PCT Pub. Date: Nov. 17, 2016

(65) Prior Publication Data
US 2018/0022890 A1 Jan. 25, 2018

(30) Foreign Application Priority Data
May 14, 2015 (KR) .......................... 10-2015-0067549

(51) Int. Cl.
*C08K 5/12* (2006.01)
*C07C 69/82* (2006.01)
*C08K 5/00* (2006.01)

(52) U.S. Cl.
CPC ............... *C08K 5/12* (2013.01); *C07C 69/82* (2013.01); *C08K 5/0016* (2013.01)

(58) Field of Classification Search
CPC ............ C07C 69/80; C07C 69/82; C08K 5/12
See application file for complete search history.

(56) References Cited

U.S. PATENT DOCUMENTS

| | | | |
|---|---|---|---|
| 4,620,026 A | 10/1986 | Siegel | |
| 8,329,796 B2 * | 12/2012 | Grass ..................... | C08K 5/12 524/321 |
| 9,127,141 B2 * | 9/2015 | Lee ........................ | C08K 5/12 |
| 10,150,727 B2 * | 12/2018 | Kim ........................ | C07C 67/08 |
| 2014/0336294 A1 | 11/2014 | Kim et al. | |
| 2014/0336319 A1 | 11/2014 | Kim et al. | |
| 2014/0336320 A1 | 11/2014 | Lee et al. | |
| 2015/0025186 A1 | 1/2015 | Kim et al. | |
| 2016/0237244 A1 * | 8/2016 | Boeck ..................... | C07C 67/03 |

FOREIGN PATENT DOCUMENTS

| | | | |
|---|---|---|---|
| CN | 101679708 A | 3/2010 | |
| CN | 104284917 A | 1/2015 | |
| CN | 104284933 A | 1/2015 | |
| CN | 104603193 A | 5/2015 | |
| JP | 2005320302 A * | 11/2005 | |
| KR | 10-0812512 B | 3/2008 | |
| KR | 20130035493 A * | 4/2013 | |
| KR | 10-2013-0067513 A | 6/2013 | |
| KR | 10-2014-0132697 A | 11/2014 | |
| WO | WO-2008140177 A1 * | 11/2008 | ............. C07C 67/08 |

OTHER PUBLICATIONS

Machine translated English language equivalent of KR 2013035493 (2013, 8 pages).*
TGSC (*isobutyl alcohol*. TGSC Information System, 2019, 18 pages).*
TGSC (butyl alcohol, TGSC Information System, 2019, 15 pages).*
TGSC (isononanol, TGSC Information System, 2019, 4 pages).*
Machine translated English language equivalent of JP 2005-320302 (2005, 10 pages).*
"Polymer anti-aging practical manual", Institute of Synthetic Materials, Ministry of Chemical Industry, Jinhai Chemical Co., Ltd., Chemical Industry Press, Jun. 30, 1999, p. 198, (9 pages).
"Encyclopedia of Chemical Engineering", vol. 19, "Encyclopedia of Chemical Engineering" editorial board, pp. 424-425, Sep. 30, 1998, Chemical Industry Press.
"Chemistry Principles and Application Basis, vol. 3, Application Portion", the 1st edition, edited by Ding Tingzhen, pp. 120-121, Apr. 30, 1998, Higher Education Press.
"Polymer material molding and processing", the 3rd edition, edited by Tang Songchao, pp. 33-34, May 31, 2013, China Light Industry Press.

* cited by examiner

*Primary Examiner* — Brieann R Johnston
(74) *Attorney, Agent, or Firm* — Dentons US LLP

(57) ABSTRACT

The present invention relates to an ester-based plasticizer composition, a method for preparing the same and a resin composition comprising the same. The ester-based plasticizer composition according to one embodiment of the present invention is a novel terephthalate-based ester compound for a plasticizer prepared by transesterification. When the ester-based plasticizer composition used in a resin composition, it is capable of providing excellent properties such as migration resistance and volatility resistance as well as excellent resistance for stress, tensile strength and elongation rate.

15 Claims, No Drawings

ESTER-BASED COMPOUND, COMPOSITION COMPRISING THE SAME, METHOD FOR PREPARING THE SAME AND RESIN COMPOSITION COMPRISING THE SAME

FIELD OF THE INVENTION

This application is a National Stage Entry of International Application No. PCT/KR2016/005039 filed on May 12, 2016, and claims the benefit of Korean Application No. 10-2015-0067549 filed on May 14, 2015, all of which are hereby incorporated by reference in their entirety for all purposes as if fully set forth herein.

The present invention relates to an ester-based compound, a composition comprising the same, a method for preparing the same, and a resin composition comprising the same, and in particular, to an ester-based plasticizer composition comprising a terephthalate-based compound having three compositions, a method for preparing the same, and a resin composition comprising the same.

DESCRIPTION OF THE RELATED ART

In common plasticizers, alcohols react with polycarboxylic acids such as phthalic acid and adipic acid to prepare esters corresponding thereto. Commercially important examples thereof include adipate of C8, C9 and C10 alcohols, for example, di(2-ethylhexyl) adipate, diisononyl adipate and diisodecyl adipate; and phthalate of C8, C9 and C10 alcohols, for example, di(2-ethylhexyl) phthalate, diisononyl phthalate and diisodecyl phthalate.

Specifically, through a plastisol and dry mixing, the di(2-ethylhexyl) phthalate is used in preparing toys, films, shoes, paint, flooring materials, gloves, wallpapers, synthetic leather, sealants, tarpaulins, automotive floor coating materials, furniture, foaming mats and soundproof panels, and may also be used in producing PVC cable exteriors and insulators, and other calendering plasticizing PVC products.

As ester compounds currently used as a plasticizer, di-(2-ethylhexyl) phthalate (DEHP), di-isononyl phthalate (DINP), di-2-propylheptyl phthalate (DPHP) or diisodecyl phthalate (DIDP) and the like are mainly used, however, these products are harmful to human bodies due to environmental hormones disrupting the endocrine system, and depending on the application, have a limit in improving physical properties of products in terms of processability with resins, absorption rates, volatile loss, migration loss, thermal stability and the like.

Accordingly, development of ester compounds that are environmental friendly or non-phthalate-based, and capable of sufficiently improving physical properties of existing products in terms of various physical properties such as volatile loss, migration loss and thermal stability as well as processability with resins, absorption rates, hardness, tensile strength and an elongation rate, and methods for preparing the same have been required.

Meanwhile, diisononyl terephthalate has poor compatibility with PVC resins and thereby has a limit in the use despite excellent cost competitiveness, and although studies to supplement this weakness have been carried out, there hasn't been much progress so far. However, provided that physical properties of diisononyl terephthalate are improved from a new perspective, full-scale use is expected, and development of generic technology therefor has been required.

DISCLOSURE OF THE INVENTION

Technical Problem

In view of the above, the present invention provides a novel ester-based compound.

The present invention provides an ester-based plasticizer composition providing excellent properties as a plasticizer in sheet formularization and compound formularization of wires, automotive interior materials, films, sheets, tubes, wallpapers, toys, flooring materials and the like, and having excellent resistance for stress.

The present invention provides a method for preparing the ester-based plasticizer composition.

The present invention provides a resin composition comprising the ester-based plasticizer composition.

Technical Solution

One embodiment of the present invention provides an ester-based compound represented by the following Chemical Formula 1.

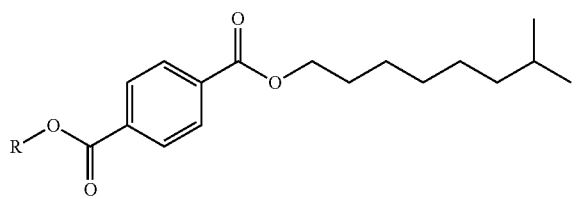

[Chemical Formula 1]

In Chemical Formula 1, R is a butyl group or an isobutyl group.

Another embodiment of the present invention provides a plasticizer composition comprising an ester-based compound represented by the following Chemical Formula 1.

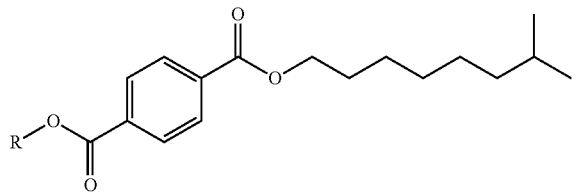

[Chemical Formula 1]

In Chemical Formula 1, R is a butyl group or an isobutyl group.

Another embodiment of the present invention provides an ester-based plasticizer composition comprising an ester-based compound represented by the following Chemical Formula 1, an ester-based compound represented by the following Chemical Formula 2 and an ester-based compound represented by the following Chemical Formula 3.

[Chemical Formula 1]

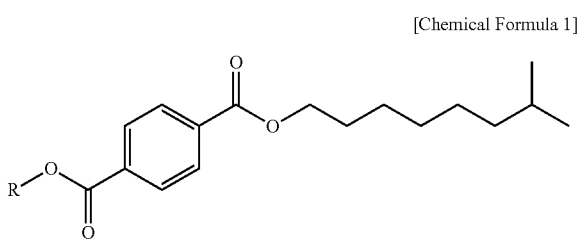

In Chemical Formula 1, R is a butyl group or an isobutyl group.

[Chemical Formula 2]

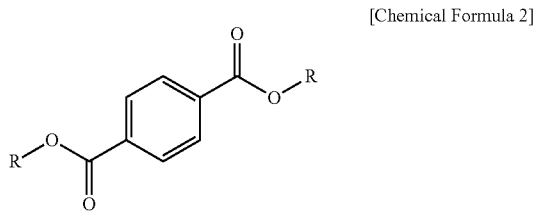

In Chemical Formula 2, Rs are each a butyl group or an isobutyl group.

Another embodiment of the present invention provides a method for preparing the ester-based plasticizer composition described above, the method including conducting transesterification of an ester-based compound represented by the following Chemical Formula 3 and an alcohol represented by the following Chemical Formula 4.

least one selected from the group consisting of ethylene vinyl acetate, polyethylene, polypropylene, polyvinyl chloride, polystyrene, polyurethane, thermoplastic elastomers and polylactic acid.

Advantageous Effects

An ester-based plasticizer composition according to one embodiment of the present invention is a novel terephthalate-based ester compound for a plasticizer prepared by transesterification, and when used in a resin composition, the ester-based plasticizer composition may provide excellent properties such as migration resistance and volatility resistance as well as excellent tensile strength and an elongation rate, and is capable of providing resin products having excellent resistance for stress.

MODE FOR CARRYING OUT THE INVENTION

Example

Hereinafter, the present invention will be described in detail with reference to examples. However, the examples

[Chemical Formula 3]

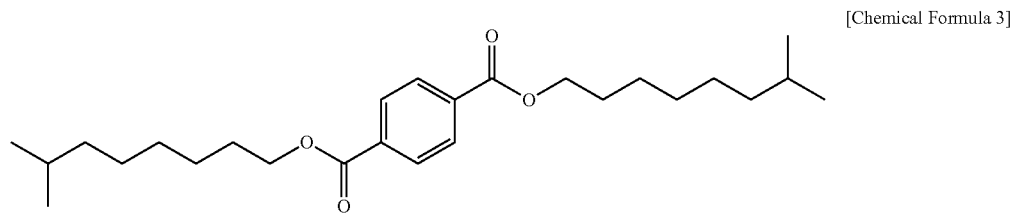 [SMILES: CC(C)CCCCCCOC(=O)c1ccc(C(=O)OCCCCCCC(C)C)cc1]

according to the present invention may be modified to various other forms, and the scope of the present invention should not be construed as being limited to the examples described below. The examples of the present invention are provided in order to more completely describe the present invention for those having average knowledge in the art.

[Chemical Formula 3]

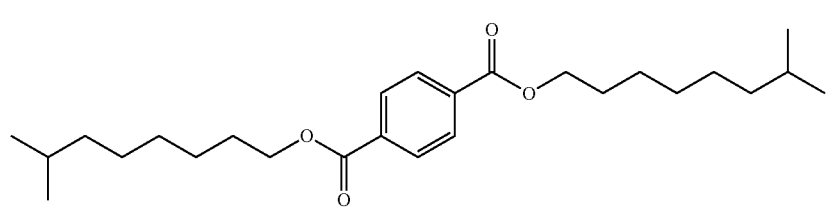

[Chemical Formula 4]

R—OH

In Chemical Formula 4, R is a butyl group or an isobutyl group.

In one embodiment, the plasticizer composition is an ether-free plasticizer.

Another embodiment of the present invention provides a resin composition comprising 5 parts by weight to 100 parts by weight the ester-based plasticizer composition described above based on 100 parts by weight of a resin comprising at Preparation Example 1: Preparation of Diisononyl Terephthalate To a 4-neck 3 liter reactor provided with a cooler, a water stripper, a condenser, a decanter, a reflux pump, a temperature controller, a stirrer and the like, 498.4 g of purified terephthalic acid (PTA), 1172.1 g of isononyl alcohol (KH Neochem) (molar ratio of terephthalic acid:isononyl alcohol was 1:3), and 1.54 g of a titanium-based catalyst (TIPT, tetra isopropyl titanate) as a catalyst (0.3 parts by weight based on 100 parts by weight of the terephthalic acid) were added, and the temperature was slowly raised up to approximately 170° C. Water started to be generated near approximately 170° C., and an ester reaction was conducted for approximately 4.5 hours while continuously adding nitrogen gas at a reaction temperature of approximately 220° C. and under atmospheric pressure, and the reaction terminated when an acid value reached 0.01.

After the reaction terminated, extractive distillation was conducted for 0.5 hours to 4 hours under reduced pressure in order to remove unreacted raw materials. Neutralization was conducted using an alkali solution after cooling the reaction solution. After that, moisture was removed by dehydrating the reaction solution. A filter medium was added to the moisture-removed reaction solution, and the result was stirred for a certain period of time and then filtered to finally prepare 1162 g of diisononyl terephthalate (yield: 99.0%).

Example 1

To a reactor provided with a stirrer, a condenser and a decanter, 2000 g of diisononyl terephthalate obtained in Preparation Example 1 and 340 g of n-butanol (17 parts by weight based on 100 parts by weight of the DINIP) were added, and then the result was conducted transesterification for 2 hours at a reaction temperature of 160° C. under nitrogen atmosphere to prepare an ester-based plasticizer composition comprising 4.0% by weight of dibutyl terephthalate (DBTP), 35.0% by weight of butylisononyl terephthalate (BINTP) and 61.0% by weight of diisononyl terephthalate (DINTP).

The reaction product went through mixed distillation to remove butanol and 2-ethylhexyl alcohol, and a final ester-based plasticizer composition was prepared.

Example 2

Transesterification was conducted in the same manner as in Example 1 except that 2000 g of diisononyl terephthalate and 340 g of isobutanol were used to finally prepare an ester-based plasticizer composition comprising 5.0% by weight of diisobutyl terephthalate, 37.0% by weight of isobutylisononyl terephthalate and 58.0% by weight of diisononyl terephthalate.

Example 3

Transesterification was conducted in the same manner as in Example 1 except that 2000 g of diisononyl terephthalate and 160 g of n-butanol were used to finally prepare an ester-based plasticizer composition comprising 2.0% by weight of dibutyl terephthalate, 25.0% by weight of butylisononyl terephthalate and 73.0% by weight of diisononyl terephthalate.

Comparative Example 1

Diisononyl terephthalate (DINTP) was used alone as a plasticizer composition.

Test Example 1: Sheet Formularization and Performance Evaluation

40 Parts by weight of each of the ester-based plasticizer compositions prepared in Examples 1 to 3, and Comparative Examples 1 and 2 was, as a plasticizer, mixed with 2.5 parts by weight of epoxidized soybean oil (ESO) and 3 parts by weight of a BZ stabilizer (BZ153T) as additives based on 100 parts by weight of a polyvinyl chloride resin (PVC (LS100S)) at 98° C. with 700 rpm. A compound was prepared by working on the result for 4 minutes at 160° C. using a roll mill, and then working on the result for 2.5 minutes (low pressure) and 2 minutes (high pressure) at 180° C. using a press.

For the sheet, hardness, tensile strength, an elongation rate, migration loss and volatile loss were measured were measured as follows, and the results are shown in the following Table 1. A stress test was also conducted and the results are shown in the following Table 2.

<Physical Property Evaluation Items>

Measurement on Hardness

Shore hardness (Shore "A") at 25° C. was measured in accordance with the ASTM D2240.

Measurement on Tensile Strength

After pulling a cross head speed at 200 mm/min using U.T.M (manufacturer; Instron, model name; 4466), a test device, in accordance with the ASTM D638 method, the spot at which the specimen was cut was measured. Tensile strength was calculated as follows:

Tensile strength (kgf/mm$^2$)=load value (kgf)/thickness (mm)×width (mm)

Measurement on Elongation Rate

After pulling a cross head speed at 200 mm/min using the U.T.M in accordance with the ASTM D638 method, the spot at which the specimen was cut was measured, and then an elongation rate was calculated as follows:

Elongation rate (%)=[length after elongation/initial length]×100.

Measurement on Migration Loss

A specimen having a thickness of 2 mm or greater was obtained in accordance with the KSM-3156, and a load of 1 kgf/cm$^2$ was applied after attaching ABS (Natural Color) on both surfaces of the specimen. The specimen was left unattended for 24 hours in a forced convection oven (80° C.), taken out, and cooled for 4 hours at room temperature. After that, the ABS attached on both surfaces of the specimen were removed, weights before and after leaving the specimen unattended in the oven were measured, and the amount of migration loss was calculated through the equation as follows.

Amount of migration loss (%)=[(initial weight of specimen at room temperature-weight of specimen after being left unattended in oven)/initial weight of specimen at room temperature]×100

Measurement on Volatile Loss

After working on the prepared specimen for 72 hours at 80° C., the weight of the specimen was measured.

Volatile loss (% by weight)=initial specimen weight−(specimen weight after working for 72 hours at 80° C.)/initial specimen weight×100.

Measurement on Heat Resistance

The degree of color changes between the initial specimen and the specimen after carrying out the volatile loss test was measured using the volatile low measurement method. The measured values were determined by the changes in the E value with respect to the L, a and b values using a colorimeter.

Stress Test

As for the stress test, the specimen was left unattended for 24 hours, 72 hours and 168 hours at room temperature as being bent, and the degree of migration (the degree of oozing) was observed and expressed as a number. The number being closer to 0 represents excellent properties.

TABLE 1

| | Hardness (Shore "A") | Tensile Strength (kg/cm²) | Elongation Rate (%) | Migration Loss (%) | Volatile Loss (%) | Heat Resistance (ΔE) |
|---|---|---|---|---|---|---|
| Example 1 | 93.5 | 236.8 | 342.8 | 1.33 | 1.19 | 1.18 |
| Example 2 | 94.0 | 239.2 | 342.0 | 1.12 | 1.41 | 1.20 |
| Example 3 | 94.7 | 238.5 | 341.9 | 1.37 | 0.85 | 1.20 |
| Comparative Example 1 | 95.3 | 235.8 | 336.1 | 1.69 | 0.59 | 1.22 |

TABLE 2

| | After 24 Hours | After 72 Hours | After 168 Hours |
|---|---|---|---|
| Example 1 | 1.0 | 2.0 | 2.0 |
| Example 2 | 1.0 | 2.0 | 2.0 |
| Example 3 | 1.0 | 2.5 | 2.0 |
| Comparative Example 1 | 1.5 | 3.0 | 3.0 |

As shown in Table 1, it was identified that the sheets using a plasticizer composition comprising i-BINTP or n-BINTP of Examples 1 to 3 exhibited enhanced elongation rate and tensile strength properties compared to the sheet of Comparative Example 1 using DINTP in the art as a plasticizer, and as shown in Table 2 listing the stress test results, it was identified that, as expressed in numbers, the plasticizer in the sheet in Comparative Example 1 continuously oozed as time passed, and had a less superior degree of migration and transformation compared to Examples 1 to 3.

Considering that the DINTP of Comparative Example 1 has fairly poor processability and has no marketability, and the DINP of Comparative Example 2 is not able to be used due to environmental problems despite excellent performance, it can be seen that performance differences between the plasticizer compositions used in the sheet preparation of Examples 1 to 3 and the plasticizer composition of Comparative Example 1 having been used in the art are significant.

Hereinafter, the present invention will be described in more detail in order to illuminate the present invention.

Terms or words used in the present specification and the claims are not to be interpreted limitedly to common or dictionary definitions, and shall be interpreted as meanings and concepts corresponding to technological ideas of the present invention based on a principle in which the inventors may suitably define the concepts of terms in order to describe the invention in the best possible way.

One embodiment of the present invention provides an ester-based compound represented by the following Chemical Formula 1.

[Chemical Formula 1]

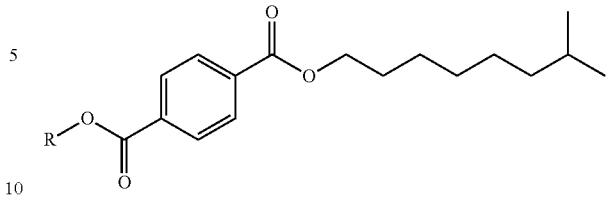

In Chemical Formula 1, R is a butyl group or an isobutyl group.

Another embodiment of the present invention provides a plasticizer composition comprising the ester-based compound represented by Chemical Formula 1.

When using a plasticizer composition comprising the ester-based compound represented by Chemical Formula 1, processing stability may be secured compared to existing plasticizers such as diisononyl terephthalate due to structural characteristics having a butyl group or an isobutyl group as one substituent of benzene, which is different from existing plasticizer compositions comprising diisononyl terephthalate, and plasticizers having excellent properties such as hardness and tensile strength, having excellent stress resistance and capable of being used in applications entirely different from existing applications may be provided.

Moreover, one embodiment of the present invention provides an ester-based plasticizer composition comprising an ester-based compound represented by the following Chemical Formula 1, an ester-based compound represented by the following Chemical Formula 2 and an ester-based compound represented by the following Chemical Formula 3:

[Chemical Formula 1]

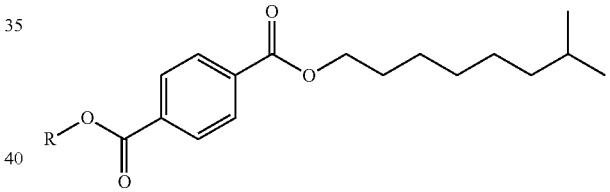

In Chemical Formula 1, R is a butyl group or an isobutyl group.

[Chemical Formula 2]

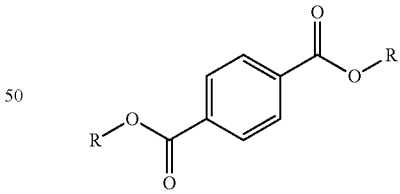

In Chemical Formula 2, Rs are each a butyl group or an isobutyl group.

[Chemical Formula 3]

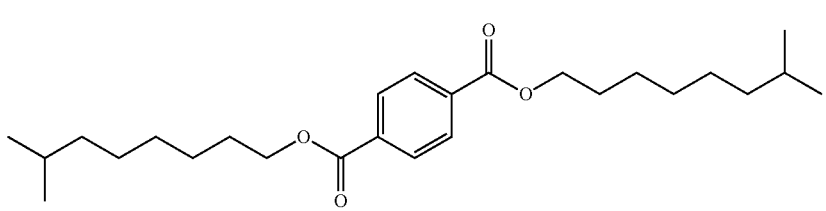

Meanwhile, the substituents Rs in Chemical Formulae 1 and 2 are the same as each other, and when R in Chemical Formula 1 is a butyl group, Rs in Chemical Formula 2 are also a butyl group, and when R in Chemical Formula 1 is an isobutyl group, Rs in Chemical Formula 2 are also an isobutyl group.

The terephthalate-based compound represented by Chemical Formula 1 according to one embodiment of the present invention is a terephthalate-based compound having ester (—COO—) groups at 1,4 positions, that is, para positions in the benzene ring, and may provide excellent physical properties such as migration resistance and volatility resistance as well as tensile strength and an elongation rate compared to phthalate-based ester compounds having ester (—COO—) groups at other positions, for example, ortho positions (1,2 positions in the benzene ring) or meta positions (1,3 positions in the benzene ring), and also may provide properties of strong resistance for stress.

When using the ester-based plasticizer composition according to one embodiment of the present invention as a plasticizer of a resin composition, an equal level of hardness, tensile strength and elongation rate compared to phthalate-based compounds normally used in existing plasticizers may be secured, and in addition to the above, volatile loss may decrease, migration resistance may be significantly superior, and resistance for stress may be excellent.

According to one embodiment of the present invention, the ester-based compound represented by Chemical Formula 1, the ester-based compound represented by Chemical Formula 2 and the ester-based compound represented by Chemical Formula 3 may be comprised in amounts of 0.5% by weight to 70% by weight, 0.5% by weight to 50% by weight and 0.5% by weight to 85% by weight, respectively, and specifically may be comprised in amounts of 10% by weight to 50% by weight, 0.5% by weight to 50% by weight and 35% by weight to 80% by weight, respectively, based on the total weight of the ester-based plasticizer composition.

According to one embodiment of the present invention, a mix ratio by weight of the sum of the non-hybrid compounds of Chemical Formulae 2 and 3 and the hybrid compound of Chemical Formula 1 may be from 95:5 to 30:70 and preferably from 90:10 to 40:60.

According to one embodiment of the present invention, by comprising the terephthalate-based compound of Chemical Formulae 1 to 3 in the above-mentioned specific weight ratio range, the ester-based plasticizer composition is capable of further improving resin processability by having an absorption rate for the resin and a short melting time while being environmental-friendly, and is capable of further improving physical properties such as hardness, tensile strength, an elongation rate, migration loss, sheet volatile loss, heat stability and accelerated weather resistance (QUV).

One embodiment of the present invention may provide a method for preparing the ester-based plasticizer composition comprising conducting transesterification of an ester-based compound represented by the following Chemical Formula 3 and an alcohol represented by the following Chemical Formula 4:

[Chemical Formula 3]

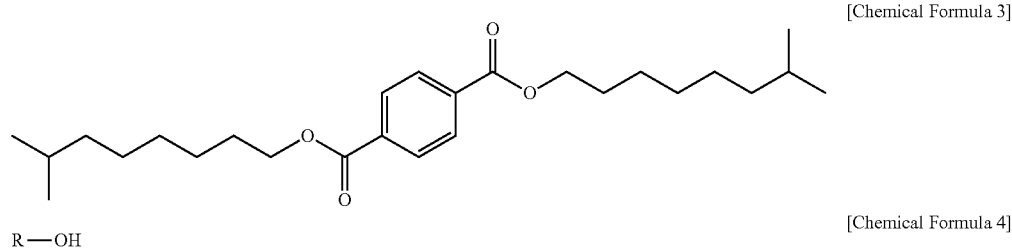

[Chemical Formula 4]

R—OH

In Chemical Formula 4, R is a butyl group or an isobutyl group.

The "transesterification" used in the present invention means a reaction in which an alcohol and an ester react to exchange R″ of the ester with R′ of the alcohol as shown in the following Reaction Formula 1 below.

[Reaction Formula 1]

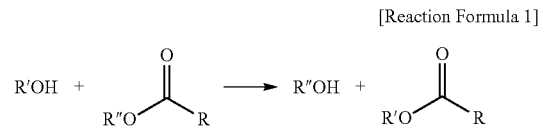

According to one embodiment of the present invention, when the transesterification is progressed, the ester-based compound represented by Chemical Formula 2 may be prepared when an alkoxide of the alcohol represented by Chemical Formula 4 attacks carbon of two ester (RCOOR″) groups present in the ester-based compound represented by Chemical Formula 3; the compound represented by Chemical Formula 1 may be prepared when an alkoxide of the alcohol represented by Chemical Formula 4 attacks carbon of one ester (RCOOR″) group present in the ester-based compound represented by Chemical Formula 3; and the compound represented by Chemical Formula 3 may remain as an unreacted portion with no reactions.

In addition, the transesterification has an advantage of not causing a problem of waste water compared to esterification between acid-alcohol, and may be progressed without a catalyst, and therefore, is capable of solving a problem caused by the use of an acid catalyst.

According to one embodiment of the present invention, the ester-based compound represented by Chemical Formula 1, the ester-based compound represented by Chemical Formula 2 and the ester-based compound represented by Chemical Formula 3 may be prepared by the transesterification in amounts of 0.5% by weight to 70% by weight, 0.5% by weight to 50% by weight and 0.5% by weight to 85% by weight, respectively, and specifically in amounts of 10% by weight to 50% by weight, 0.5% by weight to 50% by weight and 35% by weight to 80% by weight, respectively, based on the total weight of the ester-based plasticizer composition.

Being within the above-mentioned range is effective in preparing an ester-based plasticizer composition having high process efficiency, and excellent processability and absorption rate.

According to one embodiment of the present invention, the ester-based plasticizer composition prepared by the transesterification may comprise all of the ester-based compound represented by Chemical Formula 1, the ester-based compound represented by Chemical Formula 2 and the ester-based compound represented by Chemical Formula 3, and a composition ratio of the ester-based plasticizer composition may be controlled depending on the added amount of the alcohol represented by Chemical Formula 4.

According to one embodiment of the present invention, the added amount of the alcohol represented by Chemical Formula 4 may be 0.1 parts by weight to 89.9 parts by weight, specifically 3 parts by weight to 50 parts by weight and more specifically 5 parts by weight to 40 parts by weight based on 100 parts by weight of the compound of Chemical Formula 3.

According to one embodiment of the present invention, a mole fraction of the compound of Chemical Formula 3 participating in the transesterification may increase as the added amount of the alcohol represented by Chemical Formula 4 increases in the ester-based plasticizer composition, and accordingly, the content of the ester-based compound represented by Chemical Formula 1 and the ester-based compound represented by Chemical Formula 2 may increase in the ester-based plasticizer composition.

Corresponding thereto, the content of the compound represented by Chemical Formula 3 present unreacted tends to decrease.

According to one embodiment of the present invention, a molar ratio of the ester-based compound represented by Chemical Formula 3 and the alcohol represented by Chemical Formula 4 is, for example, 1:0.005 to 5.0, 1:0.05 to 2.5, or 1:0.1 to 1.0, and being within this range is effective in preparing an ester-based plasticizer composition having high process efficiency and an excellent processability improving effect.

According to one embodiment of the present invention, the transesterification may be conducted for 10 minutes to 10 hours, preferably for 30 minutes to 8 hours and more preferably for 1 hour to 6 hours at a reaction temperature from 120° C. to 190° C., preferably 135° C. to 180° C. and more preferably 141° C. to 179° C. Within the above-mentioned temperature and time ranges, an ester-based plasticizer composition having a target composition ratio may be effectively obtained. Herein, the reaction time may be calculated from the time the temperature reaches the reaction temperature after raising the temperature of the reactants.

According to one embodiment of the present invention, the transesterification may be conducted under an acid catalyst or a metal catalyst, and this is effective in reducing the reaction time.

One example of the acid catalyst may comprise sulfuric acid, methanesulfonic acid, p-toluenesulfonic acid or the like, and one example of the metal catalyst may comprise organic metal catalysts, metal oxide catalysts, metal salt catalysts or metals themselves.

One example of the metal component may be any one selected from the group consisting of tin, titanium and zirconium, or a mixture of two or more types thereof.

In addition, according to one embodiment of the present invention, the method may further comprise removing unreacted alcohol and reaction byproducts, for example, the ester-based compound represented by Chemical Formula 3, by distillation after the transesterification.

One example of the distillation may comprise two-step distillation conducting separation of the alcohol represented by Chemical Formula 4 and reaction byproducts using a boiling point difference.

As another example, the distillation may be mixed distillation. This is effective in relatively stably securing the ester-based plasticizer composition in a target composition ratio. The mixed distillation means distilling butanol and reaction byproducts at the same time.

Meanwhile, the ester-based compound represented by Chemical Formula 3 used in the transesterification of the present invention may be prepared by esterification of a compound represented by the following Chemical Formula 5 with an alcohol represented by the following Chemical Formula 6 or at least one isomer of this alcohol in the presence of a catalyst:

[Chemical Formula 3]

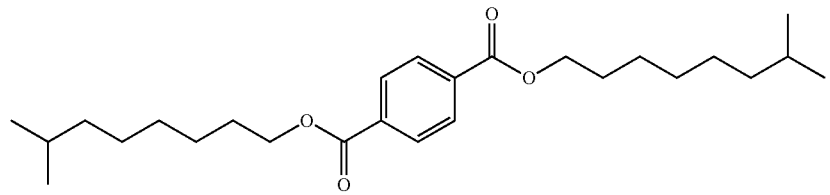

[Chemical Formula 5]

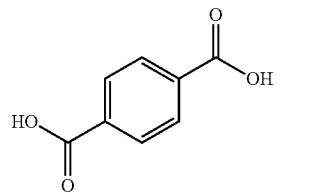

[Chemical Formula 6]

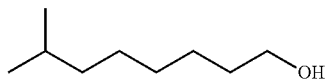

The esterification may be conducted for 10 minutes to 10 hours, preferably for 30 minutes to 8 hours and more preferably for 1 hour to 6 hours at a temperature from 80° C. to 270° C. and preferably 150° C. to 250° C. The compound of Chemical Formula 3 may be effectively prepared in the above-mentioned temperature and time ranges.

According to one embodiment of the present invention, the catalyst in the esterification may be an organic metal catalyst comprising a Sn-based or a Ti-based, an acid catalyst comprising a sulfonic acid-based or a sulfuric acid-based, or a mixed catalyst thereof, and types of the catalyst are not limited.

According to one embodiment of the present invention, the compound represented by Chemical Formula 5 and the alcohol represented by Chemical Formula 6 (or mixture of the alcohol and at least one isomer thereof) may be used in a molar ratio amount of 1:1 to 7 and preferably in a molar ratio amount of 1:2 to 5.

According to one embodiment of the present invention, the alcohol represented by Chemical Formula 6 may be prepared using common methods or commercially available products may be purchased. When using commercially available products, the alcohol represented by Chemical Formula 6 may be comprised as a mixture with at least one alcohol isomer, and the alcohol represented by Chemical Formula 6:isomers thereof may be comprised in amounts of, for example, 50 parts by weight to 100 parts by weight:0 parts by weight to 50 parts by weight, and preferably in 70 parts by weight to 100 parts by weight:0 parts by weight to 30 parts by weight.

According to one embodiment of the present invention, using the alcohol represented by Chemical Formula 6 comprising isomers may lead to the preparation of a mixture in which the ester-based compound represented by Chemical Formula 3 and isomers thereof are mixed. Accordingly, in the ester-based plasticizer composition according to one embodiment of the present invention, the compounds represented by Chemical Formulae 2 and 3, and preferably the compounds represented by Chemical Formulae 1 and 3 may each further include isomers thereof.

Through the esterification for preparing the ester-based compound represented by Chemical Formula 3 according to one embodiment of the present invention, the ester-based compound represented by Chemical Formula 3 may be prepared in a yield of approximately 80% or higher, and by conducting transesterification the ester-based compound represented by Chemical Formula 3 prepared as above and the alcohol represented by Chemical Formula 4, an ester-based plasticizer composition having a target composition may be readily prepared.

Moreover, the direct esterification, that is, the esterification used in preparing the ester-based compound represented by Chemical Formula 3 may also be used in preparing the mixed ester-based compound represented by Chemical Formula 1. In other words, the ester-based compound represented by Chemical Formula 1 may be produced by transesterification, or may be prepared by the direct esterification used in preparing the ester-based compound represented by Chemical Formula 3.

For example, in order to prepare the ester-based compound represented by Chemical Formula 1 using a direct esterification, the ester-based compound represented by Chemical Formula 1 may be prepared using terephthalic acid, the compound represented by Chemical Formula 5, isobutanol or butanol, the alcohol represented by Chemical Formula 4, and isononyl alcohol, the alcohol represented by Chemical Formula 6, as reactants.

In addition, the present invention provides a resin composition comprising the ester-based plasticizer composition and a resin.

According to one embodiment of the present invention, resins known in the art may be used as the resin. Examples thereof may comprise at least one selected from the group consisting ethylene vinyl acetate, polyethylene, polypropylene, polyvinyl chloride, polystyrene, polyurethane, thermoplastic elastomers and polylactic acid, but are not limited thereto.

According to one embodiment of the present invention, the ester-based plasticizer composition may be comprised in an amount of 5 parts by weight to 100 parts by weight based on 100 parts by weight of the resin.

According to one embodiment of the present invention, the resin composition may further include a filler.

The filler may be comprised in an amount of 0 parts by weight to 300 parts by weight, preferably in 50 parts by weight to 200 parts by weight and more preferably in 100 parts by weight to 200 parts by weight based on 100 parts by weight of the resin.

According to one embodiment of the present invention, the filler may use fillers known in the art, and is not particularly limited. Examples thereof may comprise at least one selected from the group consisting of silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate.

In addition, according to one embodiment of the present invention, the resin composition may further comprise other additives such as a stabilizer as necessary.

The other additives such as a stabilizer may be each included in, for example, in an amount of 0 parts by weight to 20 parts by weight and preferably in 1 part by weight to 15 parts by weight based on 100 parts by weight of the resin.

Examples of the stabilizer that may be used according to one embodiment of the present invention may include a calcium-zinc-based (Ca—Zn-based) stabilizer such as a complex stearic acid salt of calcium-zinc, but are not limited thereto.

In addition, according to one embodiment of the present invention, the resin composition may further include one or more types of plasticizers selected from among dioctyl phthalate (DOP), dibutyl phthalate (DBP), dioctyl terephthalate (DOTP), diisononyl phthalate (DINP), diisodecyl phthalate (DIDP) and di-(2-ethylhexyl) terephthalate (DEHTP). The plasticizer may be comprised in an amount of 0 parts by weight to 150 parts by weight and preferably 5 parts by weight to 100 parts by weight based on 100 parts by weight of the resin.

According to one embodiment of the present invention, the resin composition has sol viscosity of 4000 cp to 15000 cp, 5000 cp to 11000 cp, or 6000 cp to 9000 cp, and being within this range is effective in securing stable processability.

The sol viscosity of the present description is measured using a Brookfield (LV type) viscometer, and a spindle used is #4, and the measurement is made at 6 rpm and 12 rpm. As for the sample, for example, a plastisol is made by mixing PVC (PB900, LG Chem.) 100 phr, an ester-based plasticizer composition 75 phr, a stabilizer (KSZ111XF) 4 phr, a foaming agent (W1039) 3 phr, $TiO_2$ (TMCA100) 13 phr, $CaCO_3$ (OMYA10) 130 phr, a viscosity reducing agent (Exa-sol) 10 phr and a dispersion agent (BYK3160) 1 phr, and measurement may be conducted after storing the plastisol for 1 hour at 25° C.

The resin composition may be, for example, a resin composition lowering an amount of the introduced viscosity reducing agent compared to existing products, or without the viscosity reducing agent, that is, a viscosity reducing agent-free resin composition.

The viscosity reducing agent-free composition of the present invention means not comprising a viscosity reducing agent for controlling viscosity of the resin composition at all.

The ester-based plasticizer composition according to one embodiment of the present invention has an absorption rate for a resin and a short melting time, and thereby improves processability of the resin, and is capable of providing excellent physical properties during sheet formularization and compound formularization of wires, automotive interior materials, films, sheets, tubes, wallpapers, toys, flooring materials and the like.

What is claimed is:

1. An ester-based plasticizer composition comprising:
10% by weight to 50% by weight of au ester-based compound represented by the following Chemical Formula (1),
0.5% by weight to 50% by weight of an ester-based compound represented y the following Chemical Formula (2), and
35% by weight to 85% by weight of an ester-based compound represented by the following Chemical Formula (3), wherein each R the following Chemical Formulae (1) and (2) is an isobutyl group:

[Chemical Formula 1]

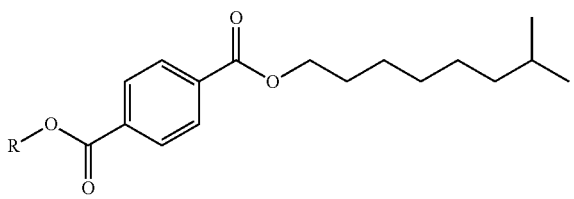

[Chemical Formula 2]

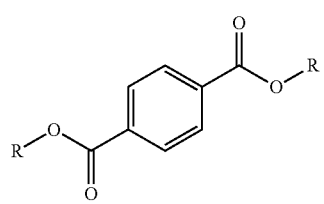

[Chemical Formula 3]

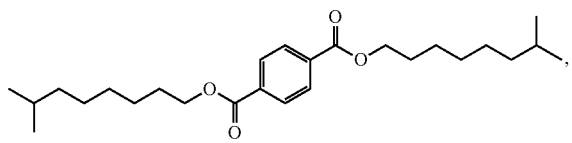

wherein a mixing ratio by weight of a sum of the ester-based compound represented by Chemical Formula (2) and the ester-based compound represented by Chemical Formula (3) to the ester-based compound represented by Chemical Formula (1) is from 90:10 to 50:50.

2. The ester-based plasticizer composition of claim 1, which is an ether-free plasticizer.

3. A method for preparing the ester-based plasticizer composition of claim 1, the method comprising conducting transesterification of an ester-based compound represented by the following Chemical Formula (3) and an alcohol represented by the following Chemical Formula (4):

[Chemical Formula 3]

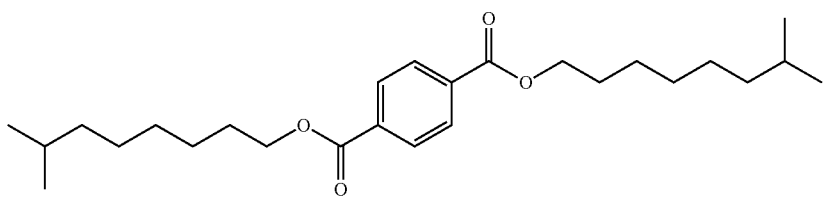

[Chemical Formula 4]

R—OH wherein, in Chemical Formula (4), R is an isobutyl group.

4. The method for preparing the ester-based plasticizer composition of claim 3, wherein a molar ratio of the compound represented by Chemical Formula (3) and the alcohol represented by Chemical Formula (4) is from 1:0.005 to 1:5.

5. The method for preparing the ester-based plasticizer composition of claim 3, wherein the alcohol represented by Chemical Formula (4) is added in an amount of 0.1 pans by weight to 89.9 parts by weight based on 100 parts by weight of the compound represented by Chemical Formula (3).

6. The method for preparing the ester-based plasticizer composition of claim 3, wherein the transesterification is conducted at a temperature from 20° C. to 190° C.

7. The method for preparing the ester-based plasticizer composition of claim 3, wherein the transesterification is a noncatalytic reaction.

8. The method for preparing the ester-based plasticizer composition of claim 3, the method further comprises removing the unreacted alcohol represented by Chemical Formula (4) and reaction byproducts by distillation after conducting the transesterification.

9. The method for preparing the ester-based plasticizer composition of claim 3, wherein part of the compound represented by Chemical Formula (3) is converted to a compound represented by the following Chemical Formula (1) and a compound represented by the following Chemical Formula (2) by the transesterification:

[Chemical Formula 1]

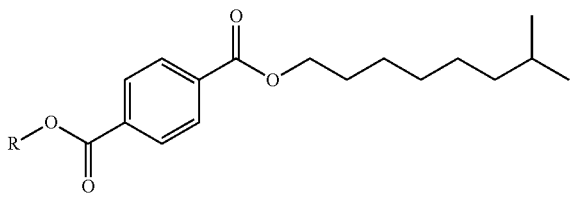

[Chemical Formula 2]

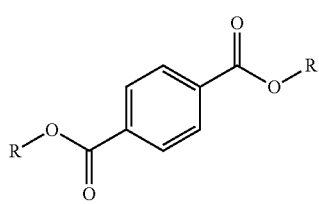

wherein R is an isobutyl group.

10. The method for preparing the ester-based plasticizer composition of claim 3, wherein the compound represented by the Chemical Formula (3) is prepared by conducting esterification of a compound represented by the following Chemical Formula (5) and an alcohol represented by the following Chemical Formula (6) in the presence of a catalyst:

[Chemical Formula 5]

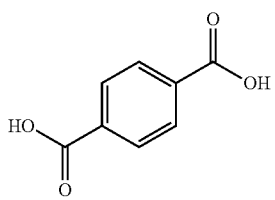

[Chemical Formula 6]

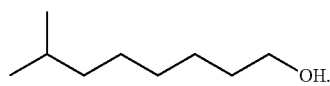

11. The method for preparing the ester based plasticizer composition of claim 10, wherein the esterification is conducted at a temperature from 80° C. to 270° C.

12. The method for preparing the ester-based plasticizer composition of claim 10, wherein the catalyst is an organic metal catalyst comprising a Sn-based or a Ti-based, an acid catalyst comprising a sulfonic acid-based or a sulfuric acid-based, or a mixed catalyst thereof.

13. The method for preparing the ester-based plasticizer composition of claim 10, wherein a molar ratio of the compound represented by Chemical Formula (5) and the alcohol represented by Chemical Formula (6) is from 1:1 to 1:7.

14. The method for preparing the ester-based plasticizer composition of claim 10, wherein the alcohol represented by Chemical Formula (6) comprises at least one isomer.

15. A resin composition comprising:
   5 parts by weight to 100 parts by weight of the ester-based plasticizer composition of claim 1 based on 100 parts by weight of a resin comprising at least one selected from the group consisting of ethylene vinyl acetate, polyethylene, polypropylene, polyvinyl chloride, polystyrene, polyurethane, thermoplastic elastomers and polylactic acid.

* * * * *